(12) United States Patent
Moses (10) Patent No.: US 7,983,435 B2
(45) Date of Patent: *Jul. 19, 2011

(54) IMPLANTABLE HEARING AID (76) Inventor: Ron L. Moses, Bellaire, TX (US)

( * ) Notice: Subject to any disclaimer, the term of this patent is extended or adjusted under 35 U.S.C. 154(b) by 1232 days.

This patent is subject to a terminal disclaimer.

(21) Appl. No.: 11/619,693

(22) Filed: Jan. 4, 2007

(65) Prior Publication Data
US 2007/0154030 A1 Jul. 5, 2007

Related U.S. Application Data (60) Provisional application No. 60/756,129, filed on Jan. 4, 2006.

(51) Int. Cl.
*H04R 25/00* (2006.01)
(52) U.S. Cl. .......................................... 381/326; 600/25
(58) Field of Classification Search .................. 381/312, 381/320, 321, 326, 328; 600/25; 623/10; 607/57
See application file for complete search history.

(56) References Cited

U.S. PATENT DOCUMENTS

| 4,957,478 | A | * | 9/1990 | Maniglia | 600/25 |
| 5,259,032 | A | * | 11/1993 | Perkins et al. | 381/312 |
| 6,137,889 | A | * | 10/2000 | Shennib et al. | 381/328 |
| 6,940,989 | B1 | * | 9/2005 | Shennib et al. | 381/326 |
| 7,668,325 | B2 | * | 2/2010 | Puria et al. | 381/322 |
| 2009/0281367 | A1 | * | 11/2009 | Cho et al. | 600/25 |

* cited by examiner

*Primary Examiner* — Fan Tsang
*Assistant Examiner* — Phylesha Dabney
(74) *Attorney, Agent, or Firm* — Haynes and Boone, LLP (57) ABSTRACT The present invention generally relates to assistive hearing devices. In one aspect, an apparatus for use in amplifying certain frequencies and canceling other frequencies is provided. The apparatus is insertable at least partially through a tympanic membrane of a user. The apparatus includes an actuator for stimulating an eardrum. The apparatus further includes an acoustic sensor for measuring a level of acoustic energy transmitted to an ear canal and/or the ear drum of the user. Additionally, the apparatus includes an electronics package for controlling the actuator and the acoustic sensor, wherein the electronics package is configured to transmit amplified selected sound waves while canceling out other sound waves having a particular frequency or frequencies. In another aspect, an apparatus for use in measuring a parameter in a body is provided. In a further aspect, a method of selectively transmitting sound waves having a predetermined frequency or frequencies is provided.

20 Claims, 4 Drawing Sheets

IMPLANTABLE HEARING AID

CROSS-REFERENCE TO RELATED APPLICATIONS

This application claims benefit of U.S. provisional patent application Ser. No. 60/756,129, filed Jan. 4, 2006, which is herein incorporated by reference.

BACKGROUND OF THE INVENTION

1. Field of the Invention

The present invention relates to assistive hearing devices. More specifically, the present invention relates to a hearing aid mounted internally to an ear.

2. Description of the Related Art

Hearing devices are well known and typically include a microphone, an amplifier and a speaker. Typically, the microphone receives a sound wave and converts the wave into an electrical signal, the amplifier amplifies the electrical signal, and the speaker converts the amplified signal into amplified sound waves that impart vibrations to the tympanic membrane or ear drum in the ear. Common hearing aids are mounted outside the ear canal, particularly around the outer ear. The externally mounted hearing aid has the advantage of accessibility to change batteries and to adjust the volume of sound. However, many users find such externally mounted hearing aides relatively bulky and objectionable for cosmetic reasons.

An alternative to externally mounted hearing aides are internally mounted hearing aids disposed in an ear canal of a user. Such internally mounted hearing aides offer better cosmetic appearance, but have disadvantages as well. For instance, the typical internally mounted hearing aid blocks the majority, if not all, of the ear canal diameter. Such blockage can cause the body of the user to produce an excessive amount of ear wax in the ear canal and can cause ear infections. Further, the blocking of the ear canal obstructs the natural transmission of sound waves through the ear canal that impact the tympanic membrane. Unless a user is totally hearing impaired, any ability of the tympanic membrane to register the natural occurring sound waves is reduced or eliminated. Thus, the user is substantially dependent upon the sound fidelity of the hearing aid. Still further, the typical internally mounted hearing aids may still be somewhat visible in the ear canal.

Some hearing systems deliver audio information to the ear through electromagnetic transducers. A microphone and amplifier transmit an electronic signal to a transducer that converts the electronic signal into vibrations. The vibrations vibrate the tympanic membrane or parts of the middle ear that transmit the sound impulses without reconverting to audio sound waves. A separate magnet can be remotely mounted at or near the tympanic membrane. The interaction between the magnetic fields of the transducer receiving the electronic signal and the magnet mounted at or near the tympanic membrane causes the magnet to vibrate and thus mechanically transmits the sound through the vibration to the ear. Typically, however, the remainder of the hearing aid is inserted into the ear canal or on the outer ear and can cause the problems discussed above. Still further, the transducers and/or magnets of the hearing aids are mounted in a relatively invasive procedure. For instance, one contact transducer having a magnet is installed by drilling through the mastoid bone, cutting through the tympanic membrane, microscopically drilling a bone structure and screwing the magnet to the malleus of the ossicular chain in the middle ear. Such procedures may be painful, expensive, and can have serious complications.

As described above, there are various types of hearing aids that are used to amplify and transmit sound waves to the hearing center of the brain resulting in the perception of sound. However, the present types of hearing aids do not selectively suppress sound waves generated by background noise and excessively loud noises while simultaneously transmitting normal speech and other desirable acoustic signals. Noise suppression could be used by astronauts on long duration missions such as the International Space Station or a Mars mission that want to selectively suppress background noise created by rotating machinery, air handling systems, and environmental control systems while still allowing the astronaut to hear the sound waves generated by other astronauts and other desirable acoustic signals. Further, the present types of hearing aides do not allow a user to amplify predetermined frequencies more than other frequencies, thereby allowing for super normal hearing of selective frequencies. Amplification of selective frequencies could be used in a military operation, wherein sound waves generated by enemy combatants could be amplified and sent to the hearing center of the brain while all other sound waves are transmitted in a normal manner. Additionally, the present types of hearing aids do not allow a user to receive signals or sound waves that are not audible to a normal person, such as in covert communication.

Therefore, there remains a need for a relatively compact hearing aid that can be inserted in the ear canal and/or through the tympanic membrane which can be used to selectively suppress sound waves generated by background noise and excessively loud noises while simultaneously hearing normal speech and other desirable acoustic signals. There is a further need for a relatively compact hearing aid which can be used to amplify predetermined frequencies greater than other frequencies, thereby allowing for super normal hearing of the predetermined frequencies. There is yet a further need for a relatively compact hearing aid which can be used to receive signals or sound waves that are not audible to a normal person.

SUMMARY OF THE INVENTION

The present invention generally relates to assistive hearing devices. In one aspect, an apparatus for use in amplifying certain frequencies and canceling other frequencies is provided. The apparatus is insertable at least partially through a tympanic membrane of a user. The apparatus includes an actuator for stimulating an eardrum. The apparatus further includes an acoustic sensor for measuring a level of acoustic energy transmitted to an ear canal and/or the ear drum of the user. Additionally, the apparatus includes an electronics package for controlling the actuator and the acoustic sensor, wherein the electronics package is configured to transmit amplified selected sound waves while canceling out other sound waves having a particular frequency or frequencies.

In another aspect, an apparatus for use in measuring a parameter in a body is provided. The apparatus is insertable at least partially through a tympanic membrane of a user. The apparatus includes a member for enhancing hearing and a sensor. The apparatus further includes an electronics package for controlling the member and the sensor, wherein the electronics package is configured to measure a temperature, a heart rate, a blood pressure, a respiratory rate, oxygenation and/or other physiologic parameters.

In a further aspect, a method of selectively transmitting sound waves having a predetermined frequency or frequencies is provided. The method includes inserting an apparatus at least partially through a tympanic membrane of a user, wherein the apparatus comprises an actuator, an acoustic sensor and an electronics package. The method further includes receiving sound waves in an ear canal of the user. The method also includes filtering out the sound waves having the predetermined frequency or frequencies from other sound waves by utilizing the electronics package. Additionally, the method includes transmitting the sound waves having the predetermined frequency or frequencies to the tympanic membrane of the user by utilizing the actuator.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION

Figure 1:
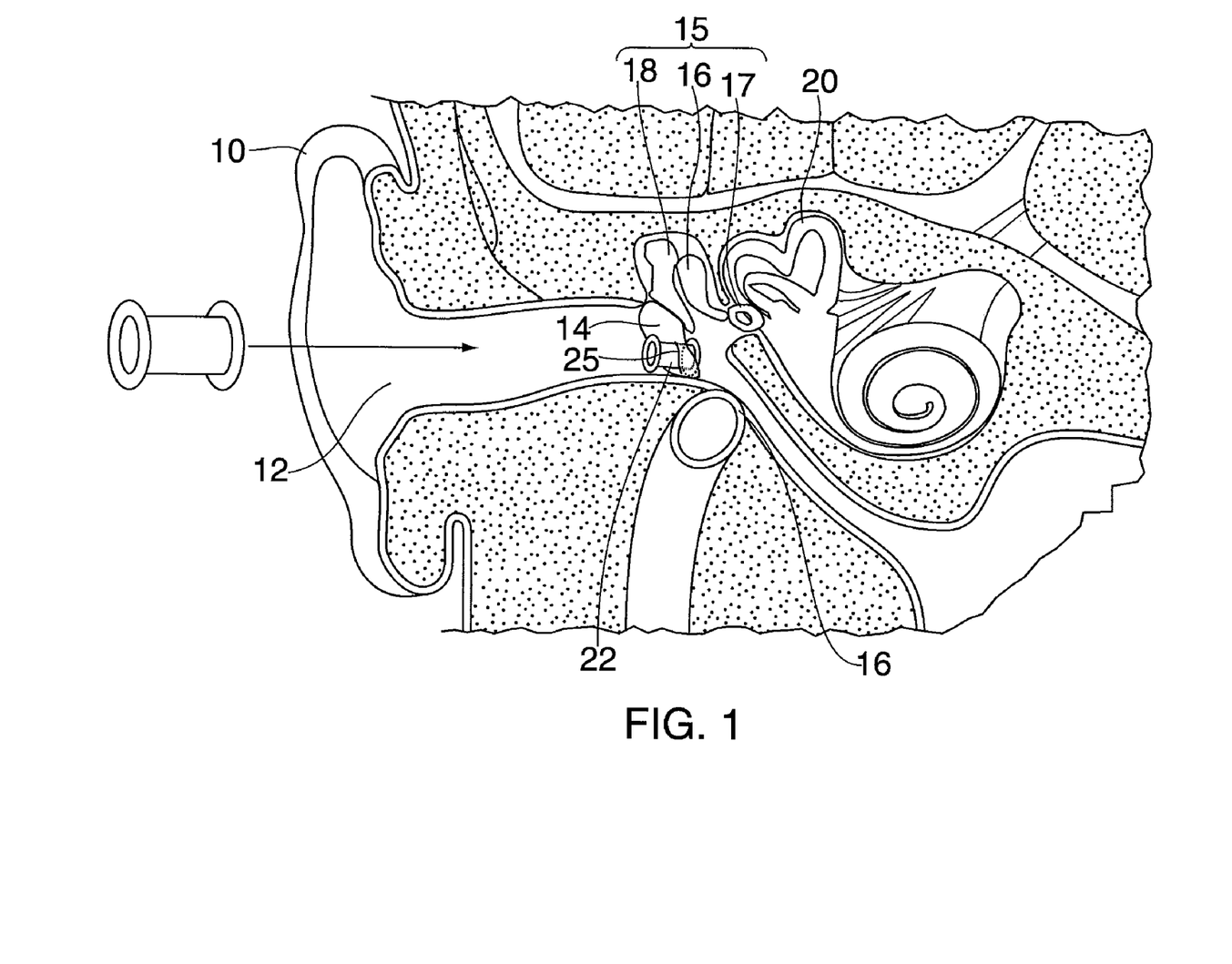
FIG. 1 is a cross-sectional schematic of an ear having the hearing aid inserted through the tympanic membrane.

FIG. 1 is a cross-sectional schematic view of a hearing aid inserted through the tympanic membrane in an ear of a user. The ear includes an outer ear 10, an ear canal 12 coupled to the outer ear 10, a tympanic membrane 14 disposed near a distal end of the ear canal 12 from the outer ear 10. An ossicular chain 15, located in a middle ear and disposed on an opposite side of the tympanic membrane 14 from the outer ear 10, couples and amplifies vibrations from the tympanic membrane 14 to an inner ear having a spiral structure known as the cochlea 20. The cochlea 20 converts the vibrations into impulses to the brain. The structure of the outer ear 10 provides a "funnel" to direct and amplify sound waves into the ear canal 12.

The hearing aid 22 of the present invention can be inserted through the outer ear 10 into the ear canal 12 and at least partially through the tympanic membrane 14. The hearing aid 22 includes a microphone, an amplifier coupled to the microphone and at least one eardrum stimulating member described in more detail below. The hearing aid 22 receives sound waves conducted from the outer ear 10 through the ear canal 12, converts the sound waves into electrical or electromagnetic signals, amplifies the signals and converts the amplified signals into amplified sound waves which is typically called a feed forward system. The amplified sound waves impact the tympanic membrane 14, and/or portions of the middle and inner ear, and vibrate the ossicular chain 15, specifically the malleus 18, the incus 16 and the stapes 17. These three bones in the ossicular chain 15 act as a set of levers that amplify the vibrations received by the tympanic membrane 14. The stapes 17 is coupled to the entrance of a spiral structure known as the cochlea 20 that contains an inner ear fluid. The mechanical vibrations of stapes 17 causes the fluid to develop fluid impulses that causes small hair-like cells (not shown) in the cochlea 20 to vibrate. The vibrations are transformed into electrical impulses which are transmitted to neuro-pathways in the hearing center of the brain resulting in the perception of sound.

Figure 2:
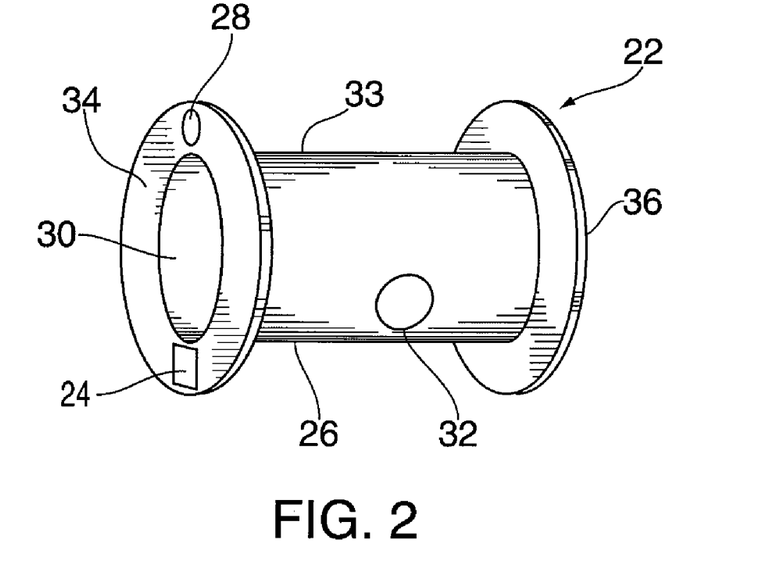
FIG. 2 is a schematic perspective view of the hearing aid.

FIG. 2 is a schematic perspective view of the hearing aid 22. The hearing aid includes a microphone 24, an amplifier 26 coupled to the microphone, at least one eardrum stimulating member 28 coupled to the amplifier and a power source 32, such as a battery. The materials that contact the tissues of the ear are preferably biocompatible, such as silicon, titanium, fluoroplastics or other materials. The microphone 24 converts the sound waves or acoustic energy into electrical or electromagnetic signals. The amplifier 26 amplifies the signals from the microphone to enhance the hearing and the eardrum stimulating member 28 stimulates the ear. The eardrum stimulating member 28 may be an actuator or a transducer. Generally, the eardrum stimulating member 28 transforms one form of energy into another form of energy. For instance, the eardrum stimulating member 28 may transform the energy and stimulate the ear through vibratory means, radio frequency means, power generation means, magnetic means, piezo-electric transducer means or any other stimulation means known in the art. In one embodiment, the eardrum stimulating member 28 reconverts the amplified signals and transduces the signals to stimulate the eardrum directly.

The microphone, amplifier and eardrum stimulating member can be inserted within a tube 33 to form a unitized assembly. Alternatively, the microphone, amplifier and/or eardrum stimulating member can be attached together to form the unitized assembly with adhesives, such as epoxy, or with mating threads or by soldering or welding or other known attachment methods. Alternatively, the microphone, amplifier and eardrum stimulating member may be housed independently and/or move independently of each other to reduce sound alteration or attenuation.

The hearing aid 22 may also include the flanges 34 and 36 disposed along the tube 33. The flanges assist in retaining the hearing aid 22 in the tympanic membrane 14. Typically, the microphone 24 would be placed on the end of the hearing aid 22 facing the outer ear canal 12. The microphone 24 can be located on a flange in the assembly of the hearing aid 22. Similarly, the eardrum stimulating member 28 can be located on a flange in the assembly. The hearing aid 22 can also include a vent hole or vent holes 30 of varying sizes and configurations formed therethrough. The vent hole 30 assists in equalizing pressures between an ear region on each side of the tympanic membrane 14. Other embodiments may not include such vent hole(s). Alternatively, one or both of the flanges can comprise the power source, such as a battery, connected to the other components of the hearing aid 22.

The microphone 24 can be a high sensitivity microphone 24. Preferably, the amplifier 26 can be a high efficiency, high gain amplifier that can amplify the sounds preferably by at least 25 dB and more preferably by at least about 45 dB. The amplifier can be assisted by the natural amplification of the outer ear 10 and the ear canal 12. A filter (not shown) can be used to filter noise and can include analog-to-digital and digital-to-analog converters. For example, analog signals from the microphone could be converted to digital signals, where digital signals are less sensitive to noise interference from extraneous transmission sources, such as mobile radio equipment, automobile telephones, and other electromagnetic waves. The digital signals could then be amplified, and the digital signals reconverted to analog signals for output through the eardrum stimulating member.

The hearing aid 22 preferably produces frequency distortions having levels no greater than about 1% at 500 Hz, 1% at 800 Hz and 0% at 1600 Hz and is preferably able to reproduce sounds from about 20 Hz to about 20 kHz. It is believed that the eardrum stimulating member will reduce the inherent attenuation of sound transmitted across air to the tympanic membrane that can occur in other hearing aids, because the eardrum stimulating member is in contact with the membrane itself. The power source 32 may advantageously be a battery, such as but not limited to a nickel-cadmium or lithium cell type battery. Preferably, the power source 32 would last at least as long as the hearing aid 22 remains inserted through the tympanic membrane 14, typically one to two years. Alternatively, the power source 32 can be a remote power source that supplies energy to the other components of the hearing aid 22 through electromagnetic radiation, such as infrared radiation waves or ultrasonic waves. In such example, the hearing aid 22 could include a remote transmitter (not shown) to transmit the energy and a receiver (not shown) attached to the hearing aid 22 to receive and convert the energy into electrical power for the components. This method could be used to recharge the battery in the hearing aid for extended periods of time. The brands and models for the components described herein are illustrative only. Other brands and/or models may also be used.

Figure 3:
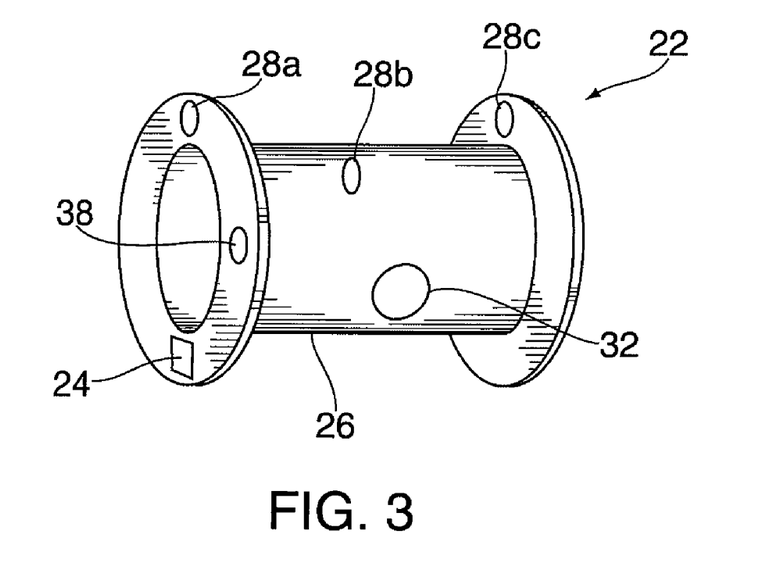
FIG. 3 is a schematic perspective view of an alternative embodiment of the hearing aid.

FIG. 3 is a schematic perspective view of an alternative embodiment of the hearing aid. Similar elements of the embodiments shown in FIGS. 2 and 3 are similarly numbered. The embodiment of FIG. 3 shows a plurality of eardrum stimulating members 28a-c. Preferably, the hearing aid 22 is partially inserted through the tympanic membrane 14, shown in FIG. 1. With such a placement, eardrum stimulating member 28a would be disposed outwardly toward the ear canal 12. Eardrum stimulating member 28c would be disposed inward of the ear canal on the inside of the tympanic membrane 14 and toward the ossicular chain 15 of the middle ear. It is believed that the eardrum stimulating member 28c may provide additional impulses in the middle ear and toward the cochlea 20 through a window in the cochlea. A middle eardrum stimulating member 28b can be disposed between eardrum stimulating members 28a and 28c for additional sound output on either side of the tympanic membrane, depending on the intersection of the hearing aid 22 with the tympanic membrane 14.

The hearing aid 22 may also include a receiver 38. The receiver 38 may be a frequency modulation (FM), amplitude modulation (AM) receiver, ultrasound receiver or other types of receivers and can have several functions. The receiver 38 may be configured to be tunable from a remote location. Further, the receiver 38 can be used to remotely control the components of the hearing aid 22, such as the amplifier 26. A remote transmitter can provide output signals to be received by the receiver 38 and adjust, for example, the amplification to avoid under or over-amplification of the converted audio signal from the microphone 24. The receiver 38 can receive information to adjust particular frequencies up or down to characterize a particular user's need. Additionally, the receiver can be used to receive transmissions from an opposite ear or from a hearing aid device in the opposite ear. The receiver can also be used to receive personal communications transmitted to the user. For instance, radio broadcasts, covert communication, personal voice messaging, and other custom input can be transmitted to the receiver 38 to be amplified and then output through the eardrum stimulating members 28a-c.

Figure 4:
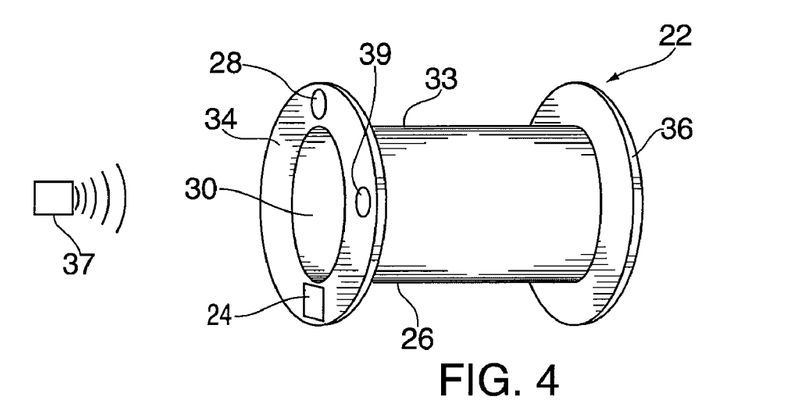
FIG. 4 is a schematic perspective view of an alternative embodiment of the hearing aid.

FIG. 4 is a schematic perspective view of an alternative embodiment of the hearing aid. Similar elements of the embodiments shown in FIGS. 2, 3 and 4 are similarly numbered. The hearing aid can be powered from a remote power source that supplies energy to the amplifier and other components of the hearing aid 22 through electromagnetic radiation, such as infrared waves. In such example, the hearing aid 22 would include a remote transmitter 37 to transmit the energy and a receiver 39 coupled to the hearing aid 22 to receive the energy and convert the energy into electrical power for the various components.

Figure 5:
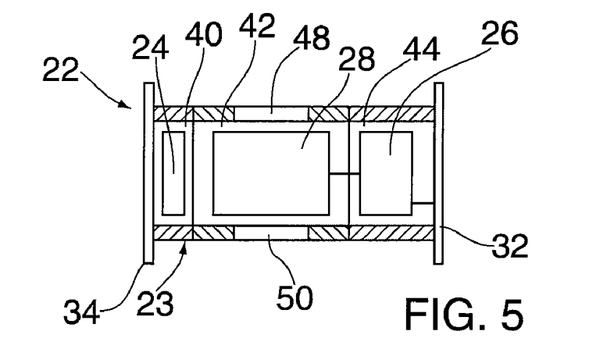
FIG. 5 is a schematic cross sectional view of an alternative embodiment of the hearing aid.

FIG. 5 is a schematic cross sectional view of an alternative embodiment of the hearing aid. Similar elements of the embodiments as shown in FIGS. 2, 3, 4 and 5 are similarly numbered. The hearing aid 22 can be assembled into a unit 23 that resists vibrational effects resulting from the movement of the tympanic membrane on at least one member of the components including the microphone 24, amplifier 26 and eardrum stimulating member 28. It is believed that such an arrangement may reduce sound distortion or attenuation caused by the relative movement of the components with the tympanic membrane to which the hearing aid is coupled, similar to the well known Doppler effect that causes an apparent change in the frequency of waves from relative motion between a sound source and a sound receiver. FIG. 5 provides one exemplary embodiment of a vibration dampening unit.

A flange 34 is coupled to a chamber 40 that houses a microphone 24. The chamber 40 is coupled to a chamber 42 that houses the eardrum stimulating member 28. The chamber 42 is coupled to a chamber 44 that houses an amplifier 26. The chamber 44 is coupled to a power source 32, such as a battery. The microphone 24 is electrically coupled to the amplifier 26 and the amplifier 26 is electrically coupled to the eardrum stimulating member 28 and to the power source 32. One or more sound transmissive windows 48, 50 are coupled to the chamber 42 and allow the sound waves from the eardrum stimulating member 28 to be transmitted through the chamber 42 to the tympanic membrane, shown in FIG. 1. One or more of the chambers 40, 42 and 44 can be at least partially filled with a fluid. It is believed that the mass of the fluid and the resulting inertia of the components within the fluid can reduce the motion of the components relative to incoming sound waves to the microphone and/or outgoing sound waves from the eardrum stimulating member. Other vibration dampening effects are possible, such as use of elastic compounds instead of fluids, air suspension, gyroscopic inertia forces on components produced by rotating the components rapidly, and the other methods known to those in the art.

Figure 6:
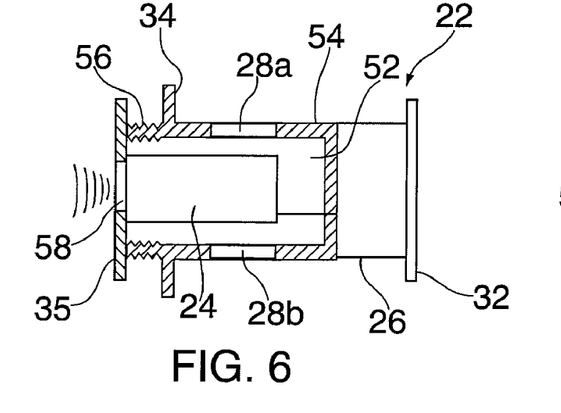
FIG. 6 is a schematic cross sectional view of an alternative embodiment of the hearing aid.

FIG. 6 is a schematic partial cross sectional view of another embodiment of the hearing aid. The hearing aid 22 includes elements previously described in reference to FIGS. 2-5 and further includes a chamber 52 for vibrational dampening, similar to the vibrational dampening aspects described in reference to FIG. 5. A flange 35 is coupled to a microphone 24. An outer shell 54 is disposed around the microphone 24, forming a chamber 52 that contains a fluid there between. The outer shell 54 is coupled to a flange 34. The flange 34 is flexibly coupled to the flange 35 by a flexible coupling 56 that is used to retain the fluid within the chamber 52. One or more openings 58 formed in the flange 35 allow sound waves to be received by the microphone 24. The outer shell 54 is coupled to an amplifier 26 disposed either within the outer shell or adjacent the outer shell. A power source 32, such as a battery, is coupled to the amplifier 26. The amplifier 26 is coupled to one or more eardrum stimulating members 28*a-b*. The eardrum stimulating members 28*a-b* can be disposed on the outer shell 54. Alternatively, the eardrum stimulating members can be disposed within the outer shell and can transmit sound through an acoustically transparent medium, such as shown in FIG. 5, to the outside of the shell.

Figure 7:
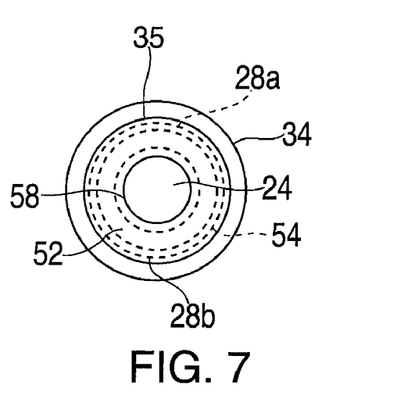
FIG. 7 is a schematic end view of the embodiment shown in FIG. 6.

FIG. 7 is a schematic end view of the embodiment shown in FIG. 6. A flange 35 is coupled to a flange 34. The flange 34 is coupled to an outer shell 54. The outer shell preferably supports eardrum stimulating members 28*a-b*. A microphone 24 is disposed radially inward of the outer shell 54 in a chamber 52. Preferably, the flange 35 has one or more openings 58 through which sound waves may be received by the microphone 24.

Figure 8:
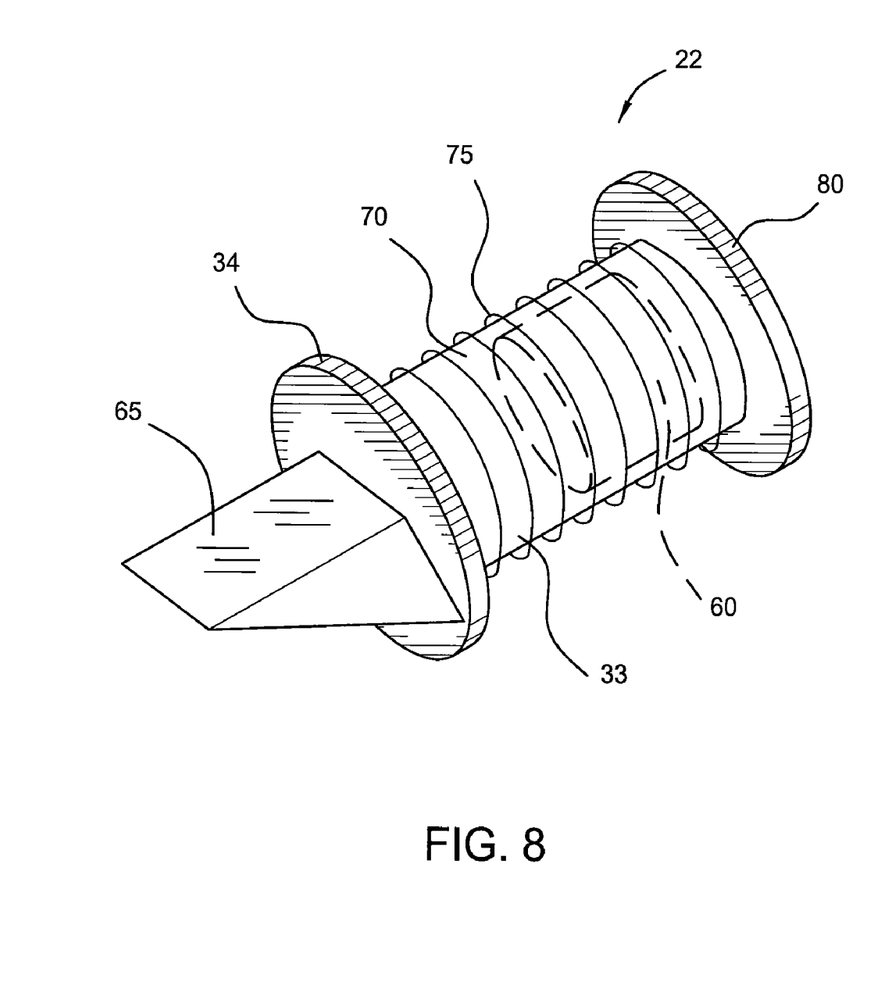
FIG. 8 is a schematic perspective view of an alternative embodiment of the hearing aid.

FIG. 8 is a schematic perspective view of an alternative embodiment of the hearing aid 22 for use in noise cancellation. The hearing aid 22 uses similar technology to the hearing aid concept previously described, except that rather than amplify sounds, the device will be used to selectively suppress background noise and excessively loud noises through noise cancellation by modification of the control algorithm and the content of the incoming frequency power spectrum. This would allow a person exposed to high levels of noise to discard cumbersome hearing protection and still be protected from high noise backgrounds while simultaneously hearing normal speech and other desirable acoustic signals.

Generally, the hearing aid 22 shown in FIG. 8 is configured to transmit sound waves while canceling out other sound waves having a predetermined frequency. In one embodiment, the hearing aid 22 includes a feed back system that would receive all the sound waves conducted from the outer ear through the ear canal but selectively suppress certain sound waves upon recognition that the sound wave is within the predetermined frequency. In another embodiment, the feed back system in the hearing aid 22 could generate a sound wave transmission that is 180 degrees phase shifted frequency of the incoming sound wave to cancel the sound wave within the predetermined frequency, thereby selectively suppressing certain sound waves. In either embodiment, the feed back system in the hearing aid 22 is adjustable, whereby the predetermined frequency may be expanded or reduced depending on a particular environment via a wireless control means or any other means. In this manner, the hearing aid 22 acts as a filter, whereby the perception of sound in the hearing center of the brain would be limited to a select group of sound waves while other sound waves in a predetermined frequency are cancelled. This embodiment may be used in a variety of applications. For example, this noise cancellation embodiment may be used in a space mission application, whereby environmental noise generated by a shuttle or a space station may be cancelled while allowing astronauts to hear the sound waves generated by the voices of other astronauts. In another example, this embodiment may be used in a military operation, whereby sound waves generated by explosions are cancelled while other normal communication sound waves are allowed to be sent to the hearing center of the brain.

As illustrated in FIG. 8, the hearing aid 22 includes an eardrum actuator 60 for stimulating the eardrum. The eardrum actuator 60 will provide direct mechanical excitation of the eardrum, thereby being more energy efficient, since energy is not wasted in the conversion from sound to vibration of the eardrum. Reduced excitation energy will then yield a simpler device with smaller actuator size, smaller battery, etc. In one embodiment, the eardrum actuator 60 utilizes Micro-Electro-Mechanical-Systems (MEMS) based actuators and/or piezoelectric devices. In another embodiment, the hearing aid 22 may include a plurality of actuators. In this embodiment, one of the actuators may be positioned external to the tympanic membrane and/or one of the actuators may be positioned internal to the tympanic membrane.

The hearing aid 22 also includes an acoustic sensor element 65 to measure the level of acoustic energy to which the eardrum is being exposed. As illustrated, the acoustic sensor element 65 is mounted in a transverse orientation relative to the hearing aid 22. It should be understood, however, that the acoustic sensor element 65 may be mounted in any position on the hearing aid 22, without departing from principles of the present invention. In another embodiment, the eardrum itself may be used as an acoustic sensor element. By measuring the displacement of the tympanic membrane, an accurate representation of the perceived sound level can be determined. The hearing aid 22 further includes an electronics package 70 for controlling the different components of the hearing aid 22. In one embodiment, the electronics package 70 may include a custom integrated circuit or a hybrid device. In another embodiment, the electronics package 70 may be configured to dampen vibrational movement and limit the Doppler effect.

As illustrated in FIG. 8, the hearing aid 22 includes a coil 75. The coil 75 has multiple functions. For example, the coil 75 may be used to charge a power source 80 by inductively coupling energy to the device through the coil 75 from an outside source. In another example, the coil 75 may be used to receive communication signals for the operator, which will be converted to mechanical vibrations of the eardrum to be interpreted as sound. In yet another example, the coil 75 may be used to provide digital communication with the device for changing operating modes, etc. In a further example, the coil 75 may be used to provide data transmission capability by means of modulating the coil impedance, similar to RFID tags and Smartcards. This passive communication technique will minimize use of the implanted device battery as physiological data is communicated to the interrogating device.

The hearing aid 22 further includes the power source 80. In one embodiment, the power source 80 is rechargeable, such as a rechargeable battery. The power source 80 may be recharged by a power transmission configuration, wherein an alternating magnetic field produced by a charger (not shown) would induce an A/C current in the coil 75, which can be rectified and used to charge the power source 80. The power source 80 may also be charged by a power scavenging configuration, wherein energy available in the environment would be scavenged to charge the power source 80. It should be understood, however, that the power source 80 may be charged in any manner, without departing from principles of the present invention. In another embodiment, the hearing aid 22 may include a housing (not shown) with a component that is configured to dampen vibrational movement and limit the Doppler Effect. The component may be a microphone, an amplifier, an actuator or combinations thereof.

In another embodiment, the hearing aid 22 may be used to amplify certain frequencies to allow for super normal hearing of certain frequencies. In this embodiment, the hearing aid 22 is configured to amplify a predetermined frequency greater than the amplification of other frequencies. The hearing aid 22 includes a feed forward system that transmits sound waves to the hearing center of the brain for normal hearing as previously discussed. In addition to the feed forward system, the hearing aid 22 includes a feed back system configured to recognize that a sound wave is within the predetermined frequency and then increase the amplification of that particular sound wave as it is transmitted to the hearing center of the brain. In other words, the hearing aid 22 in this embodiment is configured to allow super normal hearing of predetermined frequencies. The feed back system in the hearing aid 22 is adjustable, whereby the predetermined frequency may be expanded or reduced depending on a particular environment. In this manner, the hearing aid 22 acts as a selective frequency amplifier, whereby the sound waves for normal hearing would be transmitted to the hearing center of the brain while at the same time the sound waves for a predetermined frequency would be amplified greater than the sound waves for normal hearing. This super normal hearing embodiment may be used in a variety of applications. For example, this embodiment may be used in a military operation, whereby sound waves generated by enemy combatants may be amplified while all other sound waves are transmitted in a normal manner to the hearing center of the brain. In another example, this embodiment may be used to amplify sound waves generated by covert communication while all other sound waves are transmitted in a normal manner to the hearing center of the brain.

The noise cancellation of a predetermined frequency may also be used in conjunction with the amplification of a predetermined frequency, thereby allowing the hearing center of the brain to focus on a select frequency. Additionally, the noise cancellation/selective frequency enhancing properties may improve the ability of a commercial hearing aid to amplify desired sound and diminish background noise.

In another embodiment, the hearing aid 22 may be used for covert communication. There are several different ways of receiving and transmitting sound waves generated by covert communication. For example, the hearing aid 22 may include a receiver configured to receive frequencies that are higher and/or lower than the frequency audible to a normal person, which the hearing aid 22 subsequently electronically converts into a frequency audible to the normal person. In another example, the hearing aid 22 may include a receiver configured to receive a signal such as electromagnetic force that can not be detected acoustically or by other receivers, which the hearing aid 22 subsequently converts into a vibratory motion that allows the hearing center of the brain to perceive the signal. In yet another example, the hearing aid 22 may include a receiver configured to receive an encoded message, which the hearing aid 22 subsequently decodes and transmits the message to the hearing center of the brain. In a further example, the hearing aid 22 may include a receiver configured to receive a particular frequency, such as a police radio frequency, thereby allowing a user to hear covert instructions.

In another embodiment, the hearing aid 22 may be used as a measurement device for body temperature, heart rate, blood pressure, and respiratory rate, enabling constant monitoring of the health, physical exertion, and sleep patterns of a person. The implanted hearing aid 22 is well "connected" to the eardrum tissue following the initial healing process after insertion. This intimate interface between the hearing aid 22 and the body tissue is used to acquire important physiological measurements. The data from these measurements could be transmitted wirelessly via the same inductive mechanism used for battery charging. Additionally, an accelerometer sensor element could also be included in the hearing aid 22 that would monitor the various movements of a person. Thus, periods of inactivity could be correlated with respiratory rates to more accurately determine actual sleep schedules.

Referring to FIG. 1, the hearing aid 22 can be inserted at least partially through the tympanic membrane 14 with a relatively unobtrusive surgical procedure. One exemplary procedure would include anesthetizing a portion of the membrane by inserting a drop of phenol or other fluids on the tympanic membrane 14. Alternatively, the tympanic membrane 14 can be anesthetized by injecting a localized anesthetic, such as lidocaine, into the tissues of the ear canal 12. A tubular instrument (not shown) is inserted into the ear canal 12, such as an ear speculum, to view the tympanic membrane and to provide a safe conduit for a cutting instrument. In conjunction with an operating microscope, the cutting instrument is inserted through the ear speculum and forms a small slit 25 in the tympanic membrane 14. The cutting instrument may be a knife, a laser, an ultrasonic transducer, and other cutting devices. The small incision can be done in a physician's office or on an out-patient basis with generally minimal difficulty. After the slit 25 is formed in the tympanic membrane 14, the hearing aid 22 is inserted through the ear canal 12 and at least partially through the slit 25. Preferably, the hearing aid 22 is inserted through the tympanic membrane 14 so that a portion of the hearing aid extends into the ear canal 12. The tympanic membrane 14 restrains the hearing aid 22 from becoming dislodged into the ear canal 12. A portion of the hearing aid 22 that extends into the ear canal 12 provides a surface through which the microphone 24, shown in FIGS. 2-7, can receive input of sound waves through the ear canal 12. Typically, the tympanic membrane will grow and heal around the hearing aid 22. In an extended period of time, such as one to two years, the tympanic membrane 14 may press the hearing aid 22 out of the membrane. Further, the hearing aid 22 may be secured to the tympanic membrane 14, to a ring on the tympanic membrane (not shown), known as a tympanic membrane annulus, or to the ear canal 12. Due to the relatively noninvasive and simplified procedure, the hearing aid 22 can be discarded and a new hearing aid inserted in much the same manner with a new battery to last for the next period of time in which the hearing aid 22 remains secured in the tympanic membrane 14. Alternatively, the same hearing may be re-inserted easily in the office with a new battery or power source.

While foregoing is directed to the preferred embodiment of the present invention, other and further embodiments of the invention may be devised without departing from the basic scope thereof, and the scope thereof is determined by the claims that follow. For instance, the receivers can be combined into the various embodiments. The vibration dampening aspects described can be applied to any or all of the components. Further, the sequence of assembly can be varied, for example, by placing the eardrum stimulating member and receiver adjacent each other and the amplifier adjacent a power source. Thus, it is understood that the various components that coupled to each other can be connected indirectly or directly to each other.

The invention claimed is:

1. An apparatus for use in amplifying certain frequencies and canceling other frequencies, which apparatus is insertable at least partially through a tympanic membrane of a user, the apparatus comprising:
   an actuator for stimulating an eardrum;
   an acoustic sensor for measuring a level of acoustic energy transmitted to an ear canal and/or the ear drum of the user; and
   an electronics package for controlling the actuator and the acoustic sensor, the electronics package configured to transmit amplified selected sound waves while canceling out other sound waves having a particular frequency or frequencies.

2. The apparatus of claim 1, further comprising a receiver electrically coupled to the electronics package.

3. The apparatus of claim 2, wherein the receiver comprises a frequency modulated receiver.

4. The apparatus of claim 2, wherein the receiver is configured to be tunable from a remote location.

5. The apparatus of claim 4, wherein the receiver is configured to receive and transmit information regarding alterations in specific auditory frequency settings.

6. The apparatus of claim 1, further comprising a member for retaining the apparatus in the tympanic membrane.

7. The apparatus of claim 1, further comprising a plurality of actuators coupled to the electronics package.

8. The apparatus of claim 7, wherein at least one of the actuators is adapted to be external to the tympanic membrane and/or at least one of the actuators is adapted to be internal to the tympanic membrane.

9. The apparatus of claim 1, further comprising a housing with a component configured to dampen vibrational movement and limit a Doppler Effect.

10. The apparatus of claim 1, wherein the electronics package is configured to receive, amplify, and transmit signals or sound waves that are not audible to a person.

11. The apparatus of claim 1, wherein the apparatus is configured for use in covert communication.

12. The apparatus of claim 1, wherein the apparatus is configured for use in noise cancellation of a frequency or combination of frequencies.

13. The apparatus of claim 1, wherein the electronics package is configured to dampen vibrational movement and limit a Doppler Effect.

14. An apparatus for use in measuring a parameter in a body, which apparatus is insertable at least partially through a tympanic membrane of a user, the apparatus comprising: a member for stimulating an eardrum;
   a sensor for measuring an acoustic or mechanical energy from the tympanic membrane;
   and an electronics package for controlling the member and the sensor, the electronics package configured to measure a temperature, a heart rate, a blood pressure, a respiratory rate, oxygenation, other physiologic parameters or combinations thereof.

15. A method of selectively transmitting sound waves having a predetermined frequency or frequencies, the method comprising:
   inserting an apparatus at least partially through a tympanic membrane of a user, the apparatus comprising an actuator, an acoustic sensor and an electronics package;
   receiving sound waves in an ear canal of the user;
   filtering out the sound waves having the predetermined frequency or frequencies from other sound waves by utilizing the electronics package; and
   transmitting the sound waves having the predetermined frequency or frequencies to the tympanic membrane of the user by utilizing the actuator.

16. The method of claim 15, further comprising detecting acoustic and mechanical energy from the tympanic membrane.

17. The method of claim 16, wherein selectively enhanced frequencies are transmitted via the actuator back to the tympanic membrane in phase or out of phase of the acoustic and mechanical energy.

18. The method of claim 15, wherein covert communications are detected, decoded, and transmitted via the actuator to the user.

19. The method of claim 18, wherein the transmitted signal is directed to the tympanic membrane.

20. The method of claim 15, further comprising modifying the predetermined frequency or frequencies by amplifying selected frequencies or canceling other frequencies.

* * * * *